United States Patent
Krauss et al.

(10) Patent No.: US 10,315,917 B2
(45) Date of Patent: Jun. 11, 2019

(54) METHOD FOR MANUFACTURING A MICROMECHANICAL SENSOR DEVICE AND CORRESPONDING MICROMECHANICAL SENSOR DEVICE

(71) Applicant: Robert Bosch GmbH, Stuttgart (DE)

(72) Inventors: Andreas Krauss, Tuebingen (DE); Elisabeth Preiss, Rapperswil (CH)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 15/864,070

(22) Filed: Jan. 8, 2018

(65) Prior Publication Data

US 2018/0194617 A1 Jul. 12, 2018

(30) Foreign Application Priority Data

Jan. 9, 2017 (DE) .................. 10 2017 200 156

(51) Int. Cl.
*B81C 1/00* (2006.01)
*B81B 3/00* (2006.01)
*G01N 33/00* (2006.01)
*G01N 27/14* (2006.01)
*G01N 27/12* (2006.01)

(52) U.S. Cl.
CPC ........ *B81C 1/00158* (2013.01); *B81B 3/0081* (2013.01); *G01N 33/0009* (2013.01); *G01N 33/0013* (2013.01); *B81B 2201/0214* (2013.01); *G01N 27/128* (2013.01); *G01N 27/14* (2013.01)

(58) Field of Classification Search
CPC .................................................. B81C 1/00158
See application file for complete search history.

(56) References Cited

U.S. PATENT DOCUMENTS

| 7,781,850 B2 * | 8/2010 | Miles .................. B81B 3/0086 257/414 |
| 2006/0071286 A1 * | 4/2006 | Axelrod .............. G01N 29/036 257/414 |

FOREIGN PATENT DOCUMENTS

DE 3322481 A1 1/1985

OTHER PUBLICATIONS

Simon, et al.: "Micromachined metal oxide gas sensors: opportunities to improve sensor performance", Sensors and Actuators B 73 (2001), pp. 1-26.

* cited by examiner

*Primary Examiner* — Fernando L Toledo
*Assistant Examiner* — Valerie N Newton
(74) *Attorney, Agent, or Firm* — Norton Rose Fulbright US LLP; Gerard Messina (57) ABSTRACT

A micromechanical sensor device and a corresponding manufacturing method. The micromechanical sensor device is equipped with a substrate which includes a diaphragm area, multiple sensor layer areas being formed on the diaphragm area, which have a particular structured sensor layer; and a particular electrode device, via which the sensor layer areas are electrically connectable outside of the diaphragm area, the sensor layer areas being structured in such a way that they have length and width dimensions of a magnitude between 1 and 10 micrometers.

8 Claims, 6 Drawing Sheets

METHOD FOR MANUFACTURING A MICROMECHANICAL SENSOR DEVICE AND CORRESPONDING MICROMECHANICAL SENSOR DEVICE

CROSS REFERENCE

The present application claims the benefit under 35 U.S.C. § 119 of German Patent Application No. DE 102017200156.9 filed on Jan. 9, 2017, which is expressly incorporated herein by reference in its entirety.

FIELD

The present invention relates to a method for manufacturing a micromechanical sensor device and to a corresponding micromechanical sensor device.

BACKGROUND INFORMATION

Although any given micromechanical components are also usable, the present invention and its underlying problems will be described with reference to components including gas sensors based on silicon, including a heating device (hotplate).

Micro hotplates are an important component for micromechanical sensors. Micro hotplates are utilized in sensor principles which require an elevated temperature for the functional principle. Gas sensors based on the chemical transducer principle are worth mentioning, in particular: The desired chemical reaction does not yet take place at room temperature, but rather requires a certain activation energy and, therefore, an elevated operating temperature. Classical sensors of this type are, for example, metal oxide gas sensors which typically must be operated between 250° C. and 400° C.

Hot plates are utilized not only for chemical sensors, but also for sensors based on the physical transducer principle, such as, for example, thermal conductivity sensors, Pirani elements (vacuum sensors), or mass flow sensors.

Micro hotplates are manufactured, according to the related art, either as closed diaphragms or via suspended diaphragms, such as described, for example, in "Micromachined metal oxide gas sensors: opportunities to improve sensor performance," Isolde Simon et al., Sensors and Actuators B 73 (2001), pp. 1-26.

Such sensor elements including micro hotplates conventionally have typical lateral dimensions of greater than 1 mm×1 mm. In order to meet the requirements of consumer electronics, such as those present, for example, in smartphones, a miniaturization of the lateral dimensions of less than ~1 mm×1 mm is presently sought and, simultaneously, a reduction of the power consumption is required. In addition to the challenges of special heater designs, the surface area available for chip bonding is therefore becoming smaller and smaller and, therefore, the challenges placed on a production-suitable assembly and joining technology are also elevated.

Suspended diaphragms, such as those manufactured, for example, with the aid of the SMM technology, have advantages with regard to "chip handling" and bonding, since, in this case, chips may be bonded on the entire back side surface and, therefore, the possible bonding area is much larger than is the case for a diaphragm which was exposed from the back side via a wet chemical exposure (using, for example, KOH) or dry etching with the aid, for example, of DRIE. Closed diaphragms, which are typically under tensile stress, have advantages, however, with regard to robustness and compatibility with various coating methods, and therefore these closed diaphragms retain their right to exist, despite the smaller bonding area, even in highly miniaturized systems.

A combined pressure, humidity, temperature, and gas sensor was recently offered on the market. The gas sensor must be operated at elevated temperatures, for example, of approximately 200° C. to 400° C., in order to achieve a good gas reaction (catalytic conversion) and is therefore implemented in a diaphragm on a miniaturized hotplate including a heater. Typical dimensions of the hotplate-silicon substrate are 0.9×0.5 mm$^2$ in the case of a diaphragm size of 300×300 μm$^2$. The heat output of the hotplate should be optionally dimensioned in such a way that the other sensors, which are integrated together in a very small housing (for example, 3×3×0.9 mm$^3$), are not excessively affected.

The actual sensitive material of the gas sensor, whose resistance is measured, is mounted on the surface of the diaphragm, in this case, using methods known today, i.e., for example, via a dispensing method, wet-chemically manufactured materials, namely "sensor pastes," being processed herewith. This method presently imparts a limitation on a further miniaturization, since not only is the minimum size of an applied drop predefined in this case, but also usually its shape, since the material is often undesirably self-leveling.

Other methods for manufacturing gas sensors utilize ink jet methods for the deposition of the gas-sensitive material or a thin-film technology including a shadow mask for the deposition. The minimum achievable size is substantially limited in all the methods. Sizes, for example, below approximately 100×100 μm$^2$, for the dimensions of the area coated with the gas-sensitive material are not attainable.

With respect to future sensors, an application of several sensitive materials is additionally desirable. In this case, the overall size of the heated area and the diaphragm is to be further reduced. In any case, the areas on which the materials are applied must be substantially reduced in size. This is not possible by way of a drip method or even by way of an ink-jet dispensing method.

It is therefore desirable to utilize thin films, i.e., layers which are applied via physical or chemical deposition methods, for example, via chemical vapor deposition, atomic layer deposition, sputter deposition, ion beam-assisted deposition, vacuum evaporation methods, etc. (see, for example, German Patent No. DE 3 322 481 A1).

When thin-film methods are utilized for a gas-sensitive layer, it is problematic that this layer is not compatible, in many cases, with normal structuring processes of the semiconductor industry. The gas-sensitive layers are often porous and sensitive to contamination or soiling, and often even to components of lithographic varnishes.

In standard structuring methods, a layer is generally applied in a planar manner over an entire wafer, then a mask is applied with the aid of photolithography and then a restructuring of the layer is carried out in the unprotected areas with the aid of wet etching or dry etching or sputtering methods. The mask is usually made of photoresist; a multilayer mask, a so-called "hard mask," is also utilized, if necessary. These masks are removed after this structuring step. Etching methods are used again in this case, which means there is an undesirable interaction in the case of gas-sensitive layers lying under the mask.

With the aid of this standard structuring method in the semiconductor industry, structure widths in the range of a few dozen nanometers may be achieved.

The exposure of a gas-sensitive layer to the chemicals used (for example, photoresist for a resist mask, solvents for the removal of the resist mask, etchants for removing a hard mask, argon- or oxygen-ion bombardment, or the like) usually substantially changes the layer, primarily when this process must be carried out multiple times and the first deposited and structured layers are then subjected to this process multiple times. In this case, etching media or etching methods would have to be found, each of which selectively etches only the desired layer and the attack on the other gas-sensitive layers is minimal. The fact that the aforementioned metal oxides have, in part, very similar etching properties is a great challenge. In addition, the gas-sensitive layers are mostly porous. Residue of mask materials and process chemicals may therefore remain in the gas-sensitive material throughout the entire process sequence, in a barely controllable manner, and influence the subsequent gas reaction.

SUMMARY

The present invention provides a method for manufacturing a micromechanical sensor device and a corresponding micromechanical sensor device.

Preferred refinements of the present invention are described herein.

The present invention provides a micromechanical sensor device and a corresponding manufacturing method, a sequential application and structuring of multiple different gas-sensitive layers being made possible, all gas-sensitive layers being protected, in this way, as extensively and comprehensively as possible against influences of the processing and process chemicals.

The example manufacturing method according to the present invention includes the use of a protective material in multiple layers for covering sequentially deposited and structured, sensitive layers, the layers of the protective material being utilized as a lift-off layer after deposition and structuring of all sensitive layers. Therefore, all gas-sensitive layers may be exposed at the end of the production process in only one step and with the aid of a controllable exposure using only one process chemical. Due to this type of manufacturing, sensor layer areas may be structured in such a way that they have defined length and width dimensions of a magnitude between 1 and 10 micrometers, which allows for a considerable further miniaturization as compared to known dispensing or ink-jet methods. In dispensing and ink-jet methods, the material to be applied is liquid and often self-leveling; as a result, during spreading, not only is the dimension of the applied layer limited in the downward direction, but the shape of the gas-sensitive layer is also often predefined in the lateral and vertical directions and is only slightly influenceable. In contrast, the manufacturing method according to the present invention allows the layers to be present in a homogeneous layer thickness and allows the shape of the sensor layer area to be arbitrarily selected.

According to one preferred refinement of the present invention, the electrode devices are connected to corresponding electrical terminal pads situated on the substrate outside of the diaphragm area. In this way, a simple and robust electrical contacting may be implemented.

According to yet another preferred refinement of the present invention, a heating device is provided in or on the diaphragm area. The elevated operating temperature necessary for the desirable chemical reaction may be adjusted in this way.

According to yet another preferred refinement of the present invention, the sensor layer areas are gas sensor areas including a respective structured, gas-sensitive sensor layer made of a metal oxide. Exemplary sensors of this type are, for example, metal oxide gas sensors which are typically operated between 250° C. and 400° C.

According to yet another preferred refinement of the present invention, the respective electrode device includes corresponding electrical strip-conductor pairs situated on the diaphragm area, which are structured in such a way that they include, in cross section, an edge area extending outward in a flat manner. This increases the adhesive strength for the sensor layers.

According to yet another preferred refinement of the present invention, the gas sensor areas each include a different sensor layer made of a metal oxide. A multi-gas sensor may be implemented in this way.

BRIEF DESCRIPTION OF THE DRAWINGS

Further features and advantages of the present invention are explained on the basis of specific example embodiments, with reference to the figures.

DETAILED DESCRIPTION OF EXAMPLE EMBODIMENTS

In the figures, identical or functionally identical elements are labeled using the same reference numerals.

Figure 1:
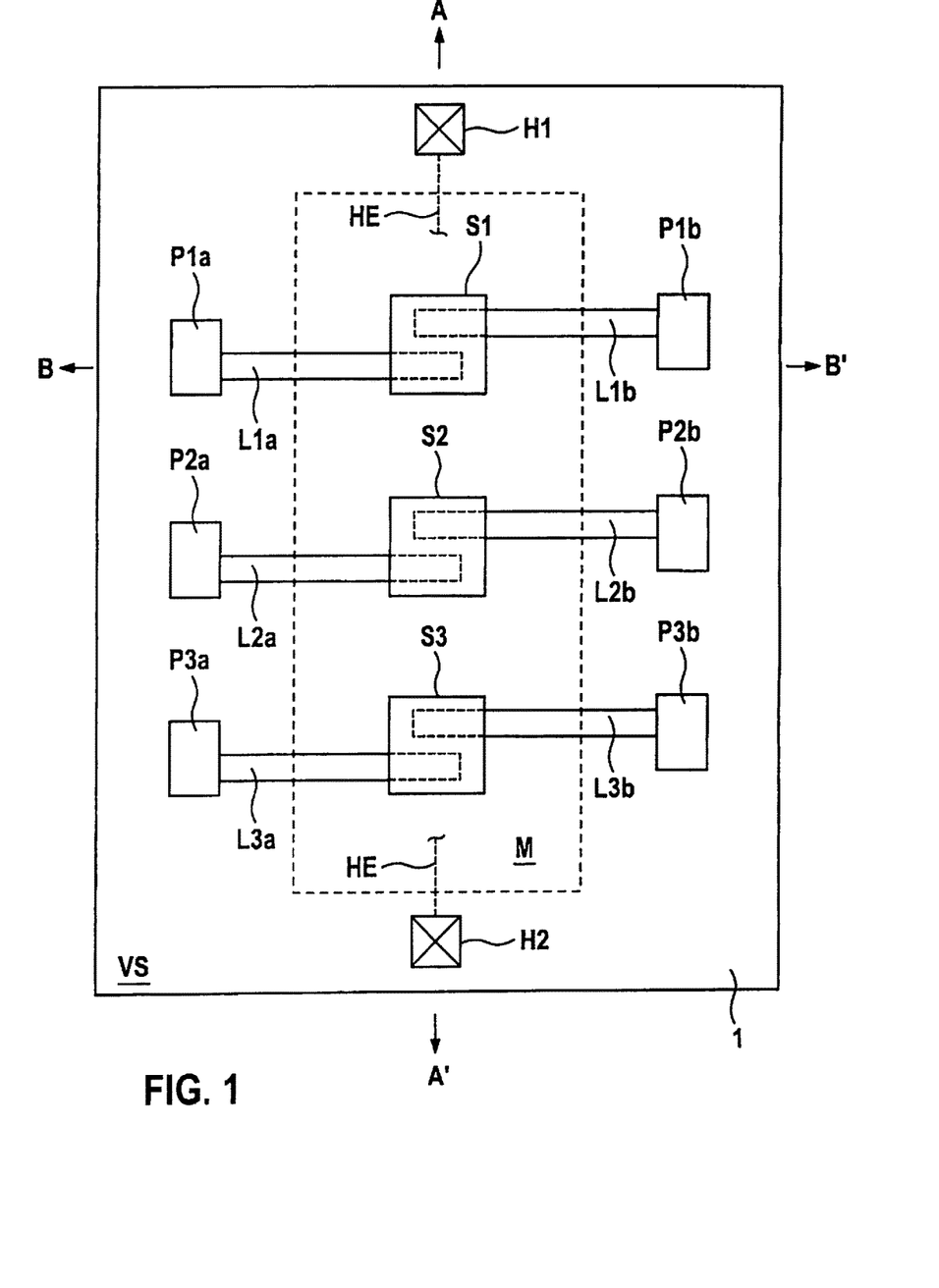
FIGS. 1 through 3 show schematic representations explaining a micromechanical sensor device according to a first specific embodiment of the present invention, in particular in FIG. 1 in a top view, in FIG. 2 along the line A-A' in FIG. 1, in FIG. 3 along the line B-B' in FIG. 1.
Figure 2:
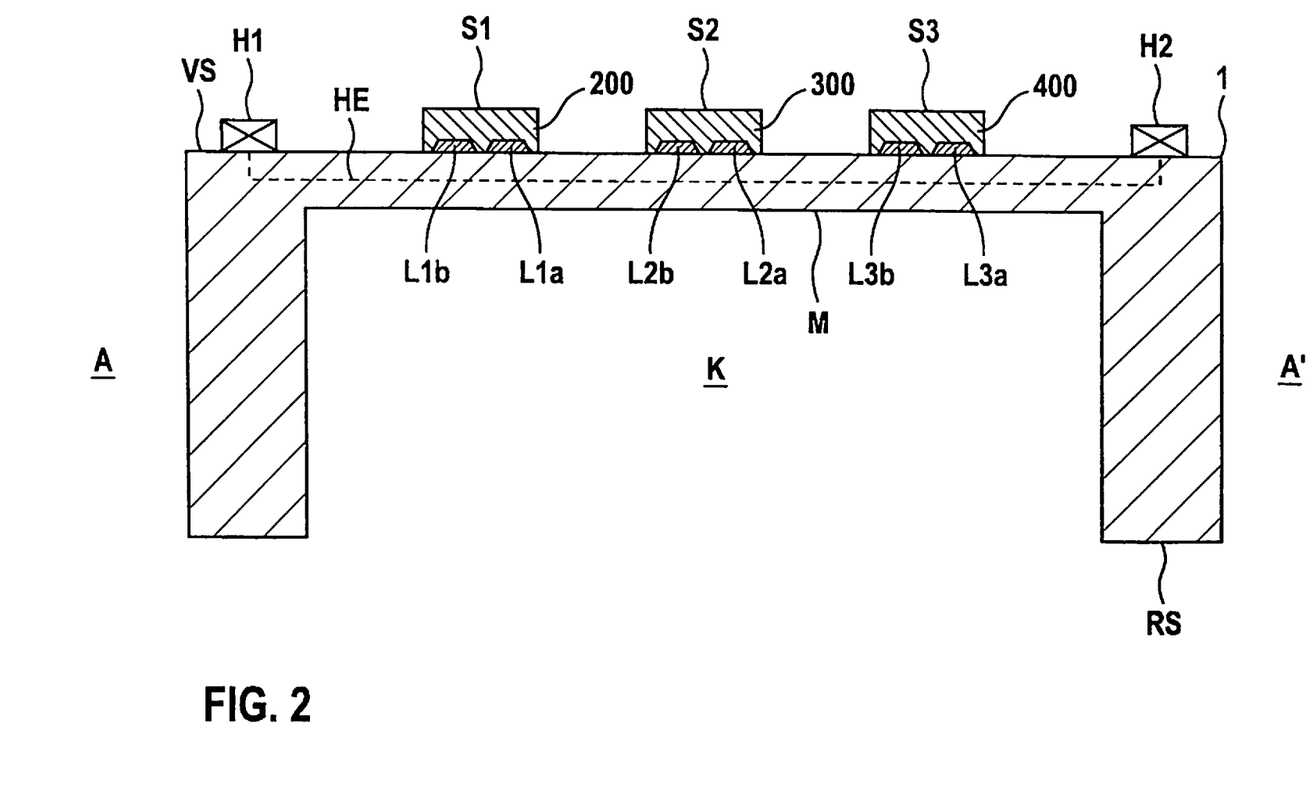
Figure 3:
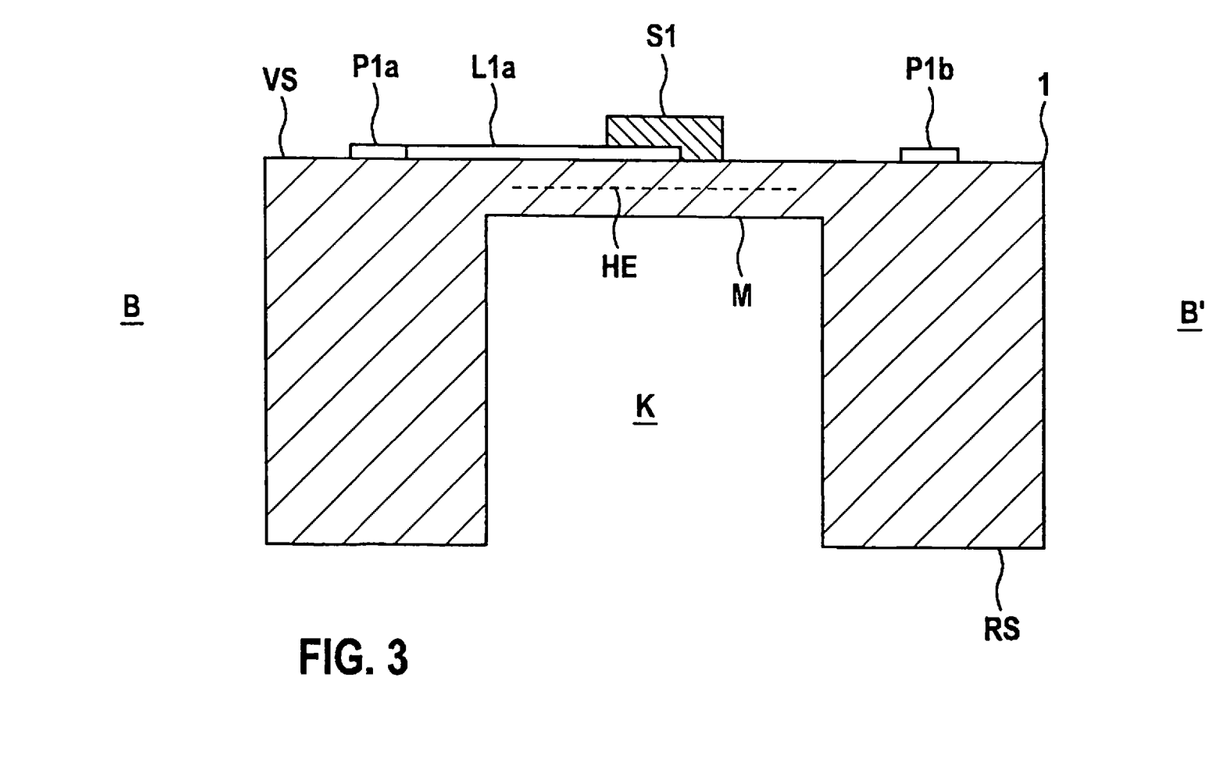

FIGS. 1 through 3 show schematic representations explaining a micromechanical sensor device according to a first specific embodiment of the present invention, in particular in FIG. 1 in a top view, in FIG. 2 along the line A-A' in FIG. 1, and in FIG. 3 along the line B-B' in FIG. 1.

In FIGS. 1 through 3, reference numeral 1 labels a substrate, for example a silicon semiconductor substrate including a front side VS and a rear side RS and including, on front side VS, a diaphragm area M above a cavity K which extends from rear side RS.

Provided on the diaphragm area are a first electrode device L1a, L1b, a second electrode device L2a, L2b, and a third electrode device L3a, L3b in the form of strip-conductor pairs which extend toward substrate 1 up to the outside of diaphragm area M on front side VS and terminate in corresponding electrical terminal pads P1a, P1b and P2a, P2b and P3a, P3b, respectively, which are provided outside of diaphragm area M on front side VS of substrate 1.

On first electrode device L1a, L1b, a first structured sensor layer area S1 which includes a first structured sensor layer 200 is formed on diaphragm area M.

On second electrode device L2a, L2b, a second structured sensor layer area S2 which includes a second structured sensor layer 300 is formed on diaphragm area M.

On third electrode device L3a, L3b, a third structured sensor layer area S3 which includes a third structured sensor layer 400 is formed on diaphragm area M.

Structured sensor layer areas 200, 300, 400 are porous gas sensor areas which are made of a metal oxide, for example, and are structured in such a way that that they include, in cross section, an edge area extending outward in a flat manner (see FIG. 2).

Typical sizes of the overall structure, in this case, are clearly less than 1×1 mm², for example 500×800 µm², having a thickness of less than 500 µm. Diaphragm area M may have a size, for example, of 300×400 µm².

A multilayer cover layer (not represented), for example, which is made, for example, of silicon oxide and silicon nitride having a typical thickness of 1 µm to 10 µm, may be provided on the top side of substrate 1 and on diaphragm area M. The cover layer (not represented) may extend across both diaphragm area M and adjacent substrate 1. Integrated into the cover layer (not represented) is a heating device HE which includes electrical terminal pads H1, H2 situated outside of diaphragm area M.

Electrical terminal pads H1, H2, P1a, P1b, P2a, P2b, P3a, P3b may be designed, for example, for wire bonding. The material of these electrical terminal pads H1, H2, P1a, P1b, P2a, P2b, P3a, P3b is, for example, a noble metal, such as, for example, gold or platinum, optionally including an adhesion promotor, such as, for example, titanium or tantalum oxide.

Heating device HE embedded into the cover layer has, for example, a meandering structure, in order to cover a preferably large portion of diaphragm area M. Heating device HE is used for heating sensor layer areas S1, S2, S3. In one alternative embodiment, it is also possible that heating device HE and electrical terminal pads H1, H2, P1a, P1b, P2a, P2b, P3a, P3b are located in a shared plane.

First, second, and third electrode devices L1a, Lib and L2a, L2b and L3a, L3b, respectively, typically have a thickness of a few dozen nm to approximately 200 nm and are structured in such a way that they include, in cross section, an edge area extending outward in a flat manner (see FIG. 2), so that the first, second, and third sensor layers 200, 300, 400 may be deposited in a highly adhesive manner. The formation of this edge area extending in a flat manner advantageously takes place with the aid of a lift-off process step.

The formation of diaphragm area M takes place, for example, by removing silicon with the aid of a DRIE process step (deep reactive ion etching) in a rear-side process step. In this case, there is no influencing of front-side sensor layers 200, 300, 400 and electrode devices L1a, L1b, L2a, L2b, L3a, L3b as well as electrical terminal pads P1a, P1b, P2a, P2b, P3a, P3b, H1, H2. This makes it possible for a front-side processing to initially take place and for a rear-side processing to subsequently take place.

The formation of diaphragm area M is also possible from the front side, however, for example with the aid of auxiliary holes (not represented) in diaphragm area M, through which the substrate material, for example silicon, is wet-chemically or dry etched. The process state according to FIG. 4g), for example, would lend itself to this purpose (see below).

The micromechanical sensor device designed in this way is a multi-gas sensor device, provided sensor layer areas S1, S2, S3 are made of different materials.

Due to the embodiment of the manufacturing method according to the present invention, which is described below, sensor layer areas S1, S2, S3 may be structured in such a way that the length and width dimensions have a magnitude between 1 µm and 10 µm, that the layers are present in a homogeneous layer thickness, and that the shape of the sensor layer area may be arbitrarily selected, which is not possible with the aid of previously available methods, such as, for example, dispensing or ink jet printing FIGS. 4a) through 4h) show schematic cross-sectional representations, in sections, explaining a method for manufacturing a micromechanical sensor device according to the first specific embodiment of the present invention.

Figure 4A:
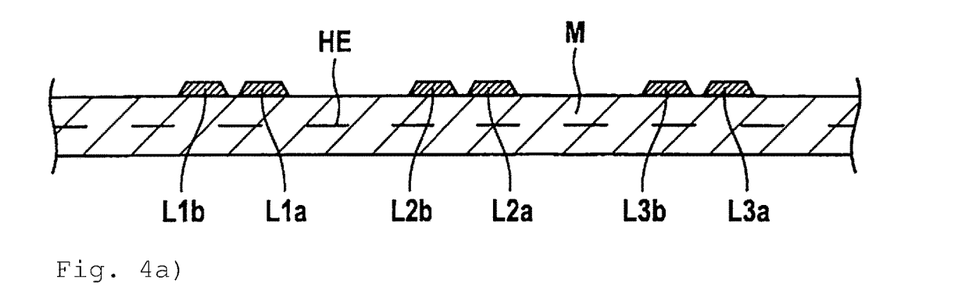
FIGS. 4a) through 4h) show schematic cross-sectional representations, in sections, explaining a method for manufacturing a micromechanical sensor device according to the first specific embodiment of the present invention.

FIGS. 4a) through 4h) only show diaphragm area M in sections, including sensor layer areas S1, S2, S3 to be formed.

FIG. 4a) shows the state after formation of first electrode device L1a, L1b, second electrode device L2a, L2b, and third electrode device L3a, L3b.

Figure 4B:
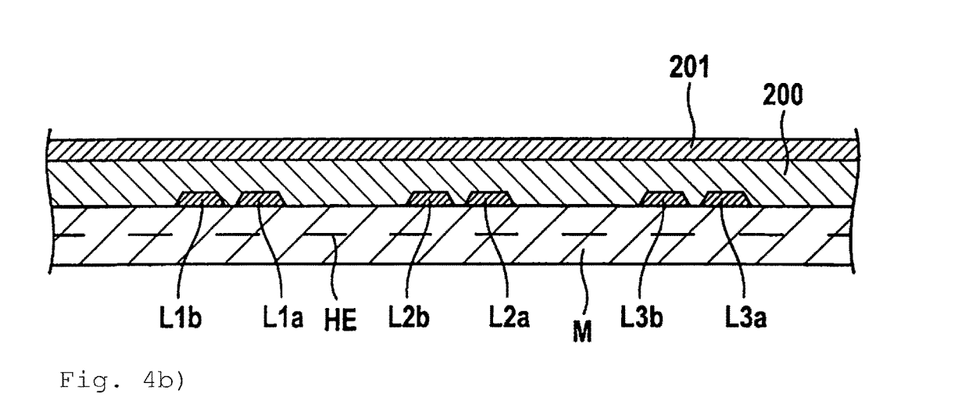

According to FIG. 4b), after the structuring of first, second, and third electrode devices L1a, L1b and L2a, L2b and L3a, L3b, respectively, and of electrical terminal pads H1, H2, P1a, P1b, P2a, P2b, P3a, P3b, a deposition of a first sensor layer 200 on the entire surface of substrate 1, and on electrode devices L1a, L1b, L2a, L2b, L3a, L3b formed thereon, takes place.

The material of first sensor layer 200 is typically a semiconducting metal oxide, for example $SnO_2$, optionally including material admixtures, such as, for example, a doping with a noble metal. First sensor layer 200 is generally not optimized with respect to good structuring, adhesion, and film properties. Instead, it is optimized mainly with respect to a good, gas-sensitive reactivity. For example, first sensor layer 200 is deposited in a porous or nanoporous form. In contrast to the local deposition of inks or pastes, the deposition method in this case yields a layer having a constant thickness and a homogeneous composition over the entire surface of a wafer and, in particular, within the subsequently structured area. Even when a shadow mask is utilized, the thickness of the deposited layer on the edge of the structure is not constant. Instead, it is reduced by way of shadowing effects.

Subsequently, a compact, dense protective layer 201 is deposited on the entire surface of first sensor layer 200, which seals the surface of first sensor layer 200 and protects it from effects of the following process steps. A lateral etching attack of first sensor layer 200, i.e., for example in wet-chemical or isotropic processes by way of undercutting, is still possible, in principle, but it may be reduced with the aid of suitable etching parameters. This may also be countered, if necessary, by way of a suitable reserve of first sensor layer 200.

First protective layer 201 may also be designed to be thicker for lower-lying layers. The material removal for further sensor layers occurring in subsequent etching processes may be suitably taken into account.

Figure 4C:
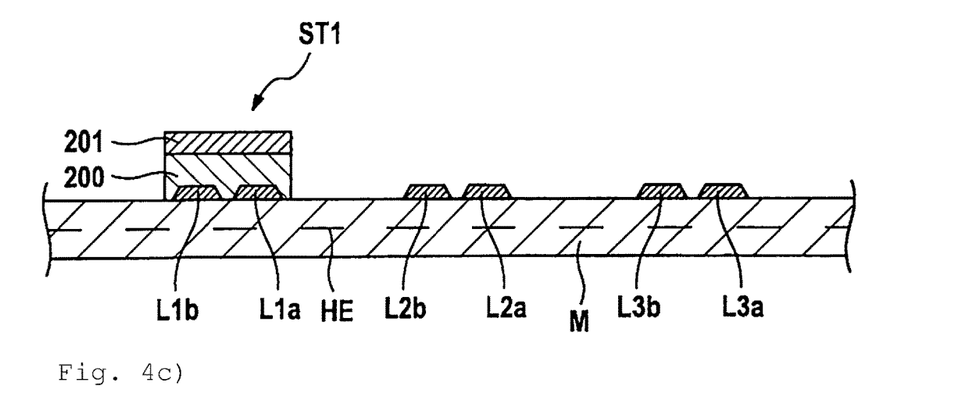

In addition, with reference to FIG. 4c), a structuring of a first stack ST1 takes place on first electrode device L1a, L1b which includes first sensor layer area S1, including first sensor layer 200, and first protective layer 201 lying over it. This structuring takes place, for example, in a photolithographic process step with the aid of a suitable photomask (not represented). By way of this photomask, an arbitrary shape (for example, rectangular having dimensions of 1 µm to 10 µm) may be predefined for the subsequently structured layer, which is not possible in the case of coating using inks or pastes, or with the aid of a shadow mask. In the structuring, remaining electrode devices L2a, L2b, L3a, L3b and surrounding areas of substrate 1 are exposed. The removal of the photoresist mask (not represented) takes place, for example, after the structuring in an oxygen plasma asking process.

Figure 4D:
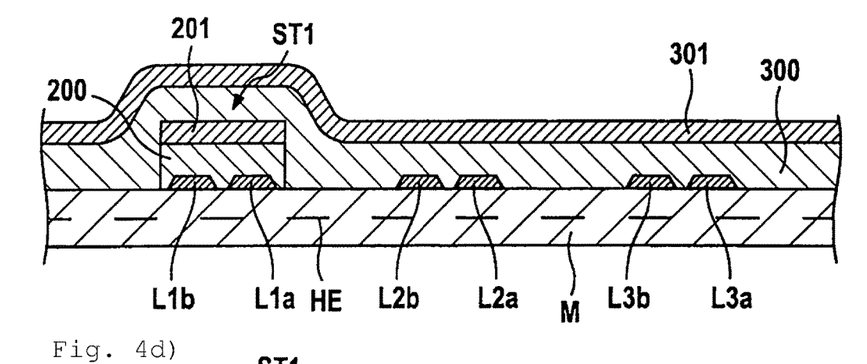

As shown in FIG. 4d), a second sensor layer 300 is deposited on the entire surface of first stack ST1 and the surrounding area of substrate 1. As is the case with first sensor layer 100, second sensor layer 300 is made of a gas-sensitive metal oxide, for example copper oxide, indium oxide, tungsten oxide, zinc oxide, or of different metal oxides, and may be doped with noble metal (see above). In this specific embodiment, second sensor layer 300 is different from first sensor layer 200, in order to therefore implement a multi-gas sensor.

Subsequent thereto, a second protective layer 301 is deposited on the entire surface of second sensor layer 300. This second protective layer 301 is preferably made of the same material or a very similar material as first protective layer 201 and is similarly utilized for protecting second sensor layer 300 in subsequent process steps.

It should be noted that the vertical dimensions are represented here in an inflated manner for the purpose of clarification and the layers usually have a ratio of nearly 1000 between the horizontal extension and the vertical extension. The layer quality and layer homogeneity around the area of first stack ST1 are irrelevant, since second sensor layer 300 and second substrate layer 301 are subsequently removed again here.

Figure 4E:
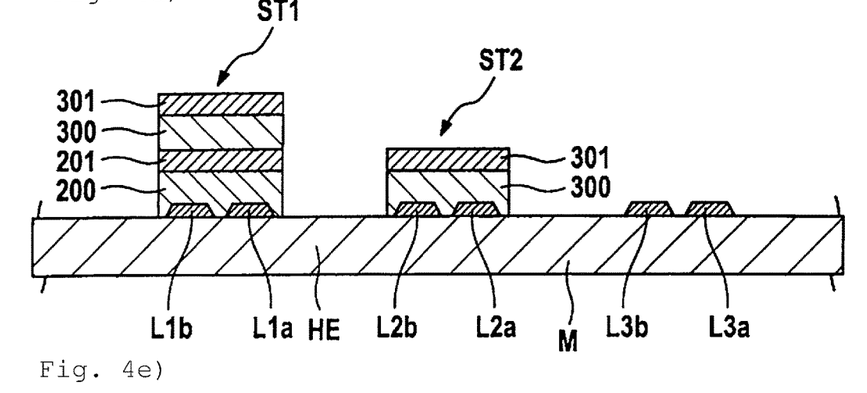

In addition, with reference to FIG. 4e), taking place in one shared process step are a simultaneous restructuring of first stack ST1 on first electrode device L1a, L1b, which now includes first sensor layer area S1 including first sensor layer 200, first protective layer 201 lying over it, second sensor layer 300, and second protective layer 301, and a structuring of a second stack ST2 on second electrode device L2a, L2b which includes second sensor layer area S1 including second sensor layer 300 and second protective layer 301 lying over it.

The two stacks ST1, ST2 are now protected from above by way of second protective layer 301.

Figure 4F:
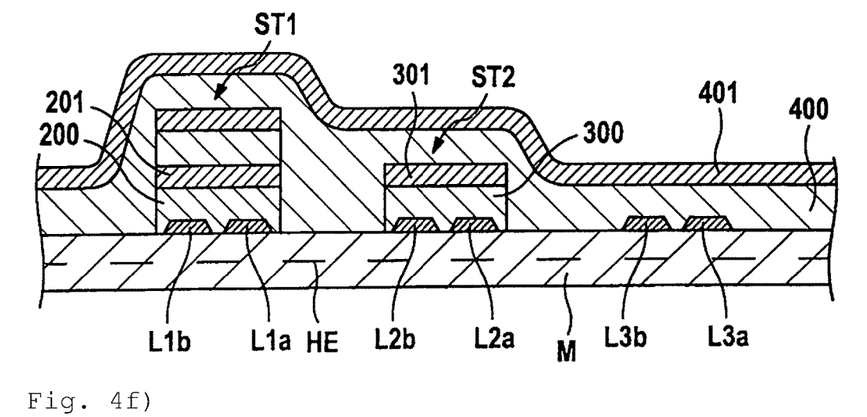

In addition, with reference to FIG. 4f), a deposition of a third sensor layer 400 onto first stack ST1, second stack ST2, and the surrounding area of substrate 1 takes place. As is the case with first sensor layer 100 and second sensor layer 300, third sensor layer 400 is made of a gas-sensitive metal oxide, for example copper oxide, indium oxide, tungsten oxide, zinc oxide, or of different metal oxides, and may be doped with noble metal (see above). In this specific embodiment, third sensor layer 400 is different from first sensor layer 200 and second sensor layer 300, in order to therefore implement a multi-gas sensor.

Subsequent thereto, a third protective layer 401 is deposited onto third sensor layer 400, which results in the process state according to FIG. 4f). The material of third protective layer 401 is preferably similar or identical to the material of first protective layer 201 and second protective layer 301 (see above).

Figure 4G:
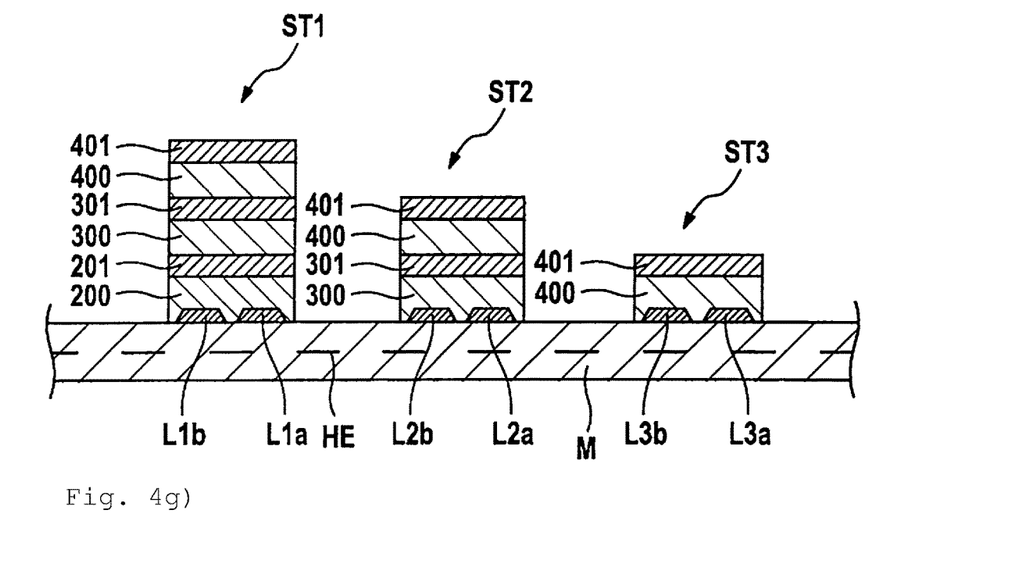

As represented in FIG. 4g), a simultaneous restructuring of first stack ST1 on first electrode device L1a, L1b which includes first sensor layer area S1 including first sensor layer 200 and first protective layer 201 lying over it, second sensor layer 300 and second protective layer 301 lying over it, and third sensor layer 400 and third protective layer 401 lying over it, and a restructuring of second stack ST2 on second electrode device L2a, L2b which includes second sensor layer area S2 including second sensor layer 300 and second protective layer 301 lying over it, third sensor layer 400 and third protective layer 401 lying over it, and a structuring of a third stack ST3 on third electrode device L3a, L3b which includes third sensor layer area S3 including third sensor layer 400 and third protective layer 401 lying over it, then take place.

Figure 4H:
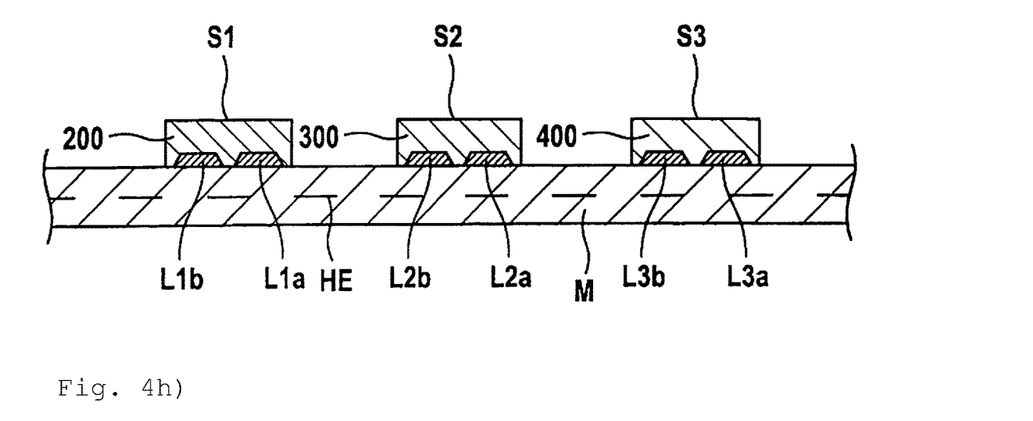

In a subsequent process step, whose result is represented in FIG. 4h), the exposure of first sensor layer area S1, second sensor layer area S2, and third sensor layer area S3 takes place. This may be advantageously carried out in a wet step, preferably with the aid of a solvent or etchant which similarly attacks first protective layer 201, second protective layer 301, and third protective layer 401. This process step is a lift-off process step, in the case where it is undesirable for first, second, and third sensor layer areas S1, S2, S3 to be attacked.

The material of first, second, and third protective layers 201, 301, 401 may be, for example, aluminum or aluminum oxide which is relatively easily structurable and readily fills and covers the layers lying thereunder. First, second, and third protective layers 201, 301, 401 may be deposited, for example, with the aid of a sputtering method.

In the case of aluminum, the etchant for removing first, second, and third protective layers 201, 301, 401 may be a highly pure, metal ion-free developer, for example based on or in a pure solution of tetramethylammonium hydroxide in water, which dissolves the aluminum due to its alkalinity. This reaction is exothermal, which additionally accelerates the attack of the developer solution on the exposed aluminum layers and ensures a good undercutting for the lift-off. Depending on process conditions, hydrogen bubbles additionally form, which may improve the desirable detachment of particular sensor layers 300 and 400 lying on top.

Alternatively, other metals or also oxides or nitrides are also usable as protective layers. In the case of the use of aluminum as protective layer material, an aluminum-compatible developer should be used already for the structuring of the photoresist in the above-mentioned photolithography step, since the protective layer outside of the resist mask could be attacked or removed otherwise already during resist structuring, which possibly results in an inhomogeneous attack on the top layer during restructuring of particular protective layer 201, 301, 401 and sensor layer 200, 300, 400.

The process state represented in FIG. 4h) then corresponds to a cut-out of the state represented in FIGS. 1 through 3.

Further optional process steps for packaging or for electrical connecting are well known in the related art and are not described further here, for the sake of simplicity.

Although the present invention is described herein on the basis of preferred exemplary embodiments, it is not limited thereto. In particular, the aforementioned materials and topologies are presented merely by way of example and are not limited to the examples described.

Although three gas sensor areas including different sensor layers for the detection of three different gases were represented and described in the aforementioned specific embodiments, the present invention is not limited thereto. Instead, the present invention is usable in arbitrary combinations of sensor layers.

Although three sensor layer areas are used in the present specific embodiment, an arbitrary plurality of sensor layer areas is possible, of course.

The heating device may also be dispensed with in certain specific embodiments.

Particularly preferred further applications for the micromechanical sensor device according to the present invention are, for example, in addition to chemical gas sensors such as metal oxide gas sensors, thermal conductivity sensors, Pirani elements, mass flow sensors, such as air mass meters, lambda sensors on micromechanical diaphragms, infrared sensor devices, strain gauges, etc.

What is claimed is:

1. A method for manufacturing a micromechanical sensor device, comprising:

providing a substrate which includes a diaphragm area;

forming multiple electrode devices on the diaphragm area, which extend to outside of the diaphragm area; and forming multiple structured sensor layer areas on a particular associated electrode device on the diaphragm area, which include a particular structured sensor layer;

wherein the following steps are carried out to form the multiple structured sensor layer areas:

depositing a first sensor layer on the substrate including the electrode devices;

depositing a first protective layer on the first sensor layer;

structuring a first stack on a first one of the electrode devices, which includes the first sensor layer area including the first sensor layer and the first protective layer lying over it;

depositing a second sensor layer on the first stack and the substrate;

depositing a second protective layer on the second sensor layer;

simultaneously restructuring the first stack on the first electrode device, which includes the first sensor layer area including the first sensor layer and the first protective layer lying over it, the second sensor layer and the second protective layer, and structuring a second stack on a second one of the electrode devices, which includes the second sensor layer area including the second sensor layer and the second protective layer lying over it; and exposing the first sensor layer area and the second sensor layer area.

2. The method as recited in claim 1, wherein, before the exposure of the first sensor layer area and the second sensor layer area, the following steps are carried out:

depositing a third sensor layer on the first stack, the second stack, and the substrate;

depositing a third protective layer on the third sensor layer;

simultaneously restructuring the first stack on the first electrode device, which includes the first sensor layer area including the first sensor layer and the first protective layer lying over it, the second sensor layer and the second protective layer lying over it, and the third sensor layer and the third protective layer lying over it, restructuring the second stack on the second electrode device, which includes the second sensor layer area including the second sensor layer and the second protective layer lying over it, and the third sensor layer and the third protective layer lying over it, and structuring a third stack on a third electrode device, which includes the third sensor layer area including the third sensor layer and the second protective layer lying over it; and thereafter, an exposure of the third sensor layer area takes place together with the exposure of the first sensor layer area and of the second sensor layer area.

3. The method as recited in claim 1, wherein the exposure is carried out with the aid of a lift-off process step, in which the first and the second protective layers are removed.

4. The method as recited in claim 2, wherein the exposure is carried out with the aid of a lift-off process step, in which the first, the second, and the third protective layers are removed.

5. The method as recited in claim 1, wherein the particular electrode device includes particular electrical strip-conductor pairs situated on the diaphragm area, which are structured in a lift-off process step in such a way that they include, in cross section, an edge area extending outward in a flat manner.

6. The method as recited in claim 1, wherein the sensor layer areas are gas sensor areas including a particular structured sensor layer made of a metal oxide, which are structured in such a way that they have length and width dimensions of a magnitude between 1 and 10 micrometers.

7. The method as recited in claim 1, wherein a formation of particular electrical terminal pads situated outside of the diaphragm area for a particular electrode device, via which the sensor layer areas are electrically connectable, takes place.

8. The method as recited in claim 2 wherein at least one of the first protective layer, the second protective layer, and the third protective layer, is made of aluminum or aluminum oxide.

* * * * *